United States Patent [19]
Emerich et al.

[11] Patent Number: 5,853,385
[45] Date of Patent: Dec. 29, 1998

[54] ENCAPSULATED PC12 CELL TRANSPLANTS FOR TREATMENT OF PARKINSON'S DISEASE

[75] Inventors: Dwaine F. Emerich, Providence, R.I.; Patrick Aebischer, Lutry, Switzerland; Jeffrey H. Kordower, Oak Park, Ill.

[73] Assignee: CytoTherapeutics, Inc., Lincoln, R.I.

[21] Appl. No.: 296,967

[22] Filed: Aug. 26, 1994

[51] Int. Cl.⁶ .................................................. A61M 31/00
[52] U.S. Cl. .............................. 604/49; 604/57; 604/93; 424/93.21
[58] Field of Search ............................... 424/93.21, 93.7, 424/404, 406, 407, 408, 499, 500, 501; 604/57, 93, 90.1, 91.1, 19, 49

[56] References Cited

U.S. PATENT DOCUMENTS 5,750,103  5/1998  Chaksey .............................. 424/93.21

FOREIGN PATENT DOCUMENTS

WO 92/19195  11/1992  WIPO .
WO 93/00127  1/1993  WIPO .
WO 93/06116  4/1993  WIPO .

OTHER PUBLICATIONS

Aebischer, Patrick, et al., "Functional Recovery in Hemiparkinsonian Primates Transplanted with Polymer–Encapsulated PC12 Cells," 126, *Experimental Neurology*, pp. 151–158 (1994).

Aebischer, Patrick, et al., "Long–Term Cross–Species Brain Transplantation of a Polymer–Encapsulated Dopamine–Secreting Cell Line," 111, *Experimental Neurology*, pp. 269–275 (1991).

Aesbsicher, Patrick, et al., "Macroencapsulation of Dopamine–Secreting Cells by Coextrusion With An Organic Polymer Solution," 12, *Biomaterials*, pp. 50–56 (1991).

Aesbicher, Patrick, et al., "Transplantation of Polymer Encapsulated Neurotransmitter Secreting Cells: Effect of the Encapsulation Technique," 113, *Journal of Biomechanical Engineering*, pp. 178–183 (1991).

Bakay, R.A.E., et al., "Biochemical And Behavioral Correction Of MPTP–Like Syndrome By Fetal Cell Transplantation", *Ann. NY Acad. Sci.*, 495, pp. 623–640 (1987).

Bankiewiez, K.S., et al., "Transient Behavioral Recovery In Hemiparkinsonian Primates After Adrenal Medullary Allografts", *Progress in Brain Research*, 78, pp. 543–550 (1988).

Bing, G., et al., "Comparison Of Adrenal Medullary, Carotid Body And PC12 Cell Grafts In 6–OHDA Lesioned Rats", *Brain Res. Bull.*, 20, pp. 399–406 (1988).

Cabasso, I., "Hollow Fiber Membranes," 12, *Encyclopedia of Chemical Technology*, 3rd Ed. Wiley, New York, (Kirk–Othmer, ed.), pp. 492–517 (1980).

Christenson, L., et al., "Tissue Reaction To Intraperitoneal Polymer Implants: Species Difference and Effects of Corticoid and Doxorubicin," *J. Biomed. Mat. Res.*, 23, pp. 705–718 (1989).

Christenson, L., "Polymer Encapsulated Thymic Stromal Tissue: Biocompatibility, Procurement and Functional Studies," Ph.D. thesis, Brown University, (1990).

Emerich, D.F., et al., "A Novel Approach To Neural Transplantation In Parkinson's Disease: Use Of Polymer–Encapsulated Cell Therapy", *Neurosci. Biobehav. Rev.*, 16, pp. 437–447 (1992).

(List continued on next page.)

*Primary Examiner*—Wynn Wood Coggins
*Assistant Examiner*—N. Kent Gring
*Attorney, Agent, or Firm*—Ivor R. Elrifi; Mintz Levin

[57] ABSTRACT

This invention relates to implantation of encapsulated PC12 cells capable of slowing or preventing the degenerative processes of Parkinson's disease by releasing factors in addition to dopamine into individuals suffering from the disease. This restorative effect continues even after the encapsulated cells are removed from the patient's brain.

3 Claims, 5 Drawing Sheets

OTHER PUBLICATIONS

Emerich, D.F., et al., "Polymer–Encapsulated PC12 Cells Promote Recovery of Motor Function in Aged Rats," 122, *Experimental Neurology*, pp.37–47 (1993).

Emerich, D.F., et al., "Transplantation of Polymer Encapsulated PC12 Cells: Use of Chitosan as an Immobilization Matrix," 2, *Cell Transplantation*, pp. 241–249 (1993).

Freed, C.R., et al., "Survival Of Implanted Fetal Dopamine Cells And Neurologic Improvement 12 to 46 Months After Transplantation For Parkinson's Disease", *New England Journal of Medicine*, 327, pp. 1549–1555 (1992).

Greene, L.A., and A.S. Tischler, "Establishment Of A Noradrenergic Clonal Line Of Rat Adrenal Pheochromocytoma Cells Which Respond To Nerve Growth Factor", *Proc. Natl. Acad. Sci. USA*, 73, pp. 2424–2428 (1976).

Grulke, Eric A., "Solubility Parameter Values," *Polymer Handbook* 3rd Ed., John Wiley & Sons, NY (J. Brandrup and E.H. Immergut, eds.), pp. 519–520 (1989).

Hyman, Carolyn, et al., "BDNF Is a Neurotrophic Factor for Dopaminergic Neurons of the Substantia Nigra," 350, *Nature*, pp. 230–232 (1991).

Jaeger, C.B., et al., "Growth of Tumor Cell Lines In Polymer Capsules: Ultrastructure of Encapsulated PC12 cells," 21, *Journal of Neurocytology*, pp. 469–480 (1992).

Jaeger, C.B., "Immunocytochemical Study of PC12 Cells Grafted to the Brain of Immature Rats," 59, *Experimental Brain Research*, pp. 615–624 (1985).

Jaeger, C.B., et al., "Polymer Encapsulated Dopaminergic Cell Lines as 'Alternative Neural Grafts,'" 82, *Progress in Brain Research*, pp. 41–46 (1990).

Langston, J. William, et al., "Core Assessment Program for Intracerebral Transplantations (CAPIT),"7, *Movement Disorders*, pp. 2–13 (1992).

Lin, Leu–Fen, et al., "GDNF: A Glial Cell Line–Derived Neurotrophic Factor for Midbrain Dopaminergic Neurons," 260, *Science*, pp. 1130–1132 (1993).

Lindsay, Ronald, et al., "Neurotrophic Factors: From Molecule To Man," 17, *TINS*, pp. 182–190 (1994).

Winn, S.R., et al., "Behavioral Recovery Following Intrastriatal Implantation of Microencapsulated PC12 Cells," 113, *Experimental Neurology*, pp. 322–329 (1991); and.

Winn, S.R., et al., "Polymer–Encapsulated Cells Genetically Modified to Secrete Human Nerve Growth Factor Promote the Survival of Axotomized Septal Cholinergic Neurons," 9, *Proc. Natl. Acad. Sci. USA*, pp. 2324–2328 (1994).

ENCAPSULATED PC12 CELL TRANSPLANTS FOR TREATMENT OF PARKINSON'S DISEASE

This application relates a method of slowing or preventing the degenerative processes of Parkinson's disease by implanting polymer-encapsulated PC12 cells into the brain of an individual suffering from the disease.

BACKGROUND OF THE INVENTION

The cardinal symptoms of Parkinson's disease, bradykinesia, postural instability, resting tremor and cogwheel rigidity are due, in large part to a comprehensive (>80%) loss of striatal dopamine principally within the putamen. This fact has led investigators to try to replace lost dopamine by grafting dopaminergic cells into the striatum. To date, fetal nigral primordia and adrenal chromaffin cells have been employed in this regard, with fetal dopaminergic neurons providing superior functional recovery in terms of both magnitude and duration of effects. J. H. Kordower et al., "Scientific basis of dopaminergic brain grafting", Therapeutic Approaches To Parkinson's Disease, (W. C. Roller and G. Paulson eds.), New York, Mercer Dekker Inc., pp.443–472 (1990). This is true for both rodent and nonhuman primate models of Parkinson's disease as well as clinical trials in patients with Parkinson's disease. (R. A. E. Bakay et al., "Biochemical And Behavioral Correction Of MPTP-Like Syndrome By Fetal Cell Transplantation", *Ann. NY Acad. Sci.,* 495, pp. 623–640 (1987); K. S. Bankiewiez et al., "Transient Behavioral Recovery In Hemiparkinsonian Primates After Adrenal Medullary Autografts", *Progress in Brain Research,* 78, pp. 543–550 (1988); C. R. Freed et al., "Survival Of Implanted Fetal Dopamine Cells And Neurologic Improvement 12 to 46 Months After Transplantation For Parkinson's Disease", *New England Journal of Medicine,* 327, pp. 1549–1555 (1992). However, the use of fetal tissue raises ethical concerns.

Pheochromocytoma (PC12) cells are another source of dopaminergic cells which have been employed as a donor tissue for transplantation. These cells are of experimental interest since they synthesize and release far more dopamine than either fetal nigral neurons or adrenal chromaffin cells. Additionally, PC12 cells are exquisitely sensitive to the trophic influences of nerve growth factor and could potentially be transformed morphologically into cells resembling neurons which could then innervate the denervated striatum. L. A. Greene, and A. S. Tischler, "Establishment Of A Nonadrenergic Clonal Line Of Rat Adrenal Pheochromocytoma Cells Which Responds To Nerve Growth Factor", *Proc. Natl. Acad. Sci. USA,* 73, pp. 2424–2428 (1976).

However, initial trials employing grafts of PC12 cells were generally unsuccessful. Short-term functional changes in unilateral 6-hydroxydopamine (6-OHDA) lesioned rats have been reported following intrastriatal PC-12 cell transplants. However, these grafts are routinely rejected within a few months following grafting. G. Bing et al., "Comparison Of Adrenal Medullary, Carotid Body And PC12 Cell Grafts In 6-OHDA Lesioned Rats", *Brain Res. Bull.,* 20, pp.399–406 (1988).

PC12 cells are a viable source of biologically delivered dopamine if they can be protected from the host immune system which appears to readily attack these cells following grafting. One method of protecting PC12 cells from the immune system is through immunoisolation. P. Aebischer et al., "Macroencapsulation Of Dopamine-Secreting Cells By Coextrusion With An Organic Polymer Solution", *Biomaterials,* 12, pp. 50–56 (1991). Grafted cells can be placed within a polymer capsule whose pores are large enough to allow bi-directional passage of nutrients into the capsule and dopamine out of the capsule; the former effect sustaining the viability of the cells and the latter potentially restoring dopamine levels depleted due to experimental lesions or idiopathic disease. In this regard, intrastriatal grafts of polymer-encapsulated PC12 cells have been demonstrated to survive and reverse drug-induced motor asymmetries in unilateral 6-ODHA-lesioned rats and alleviate the impairments in coordination and balance in normal aged rats. D. F. Emerich et al., "A Novel Approach To Neural Transplantation In Parkinson's Disease: Use Of Polymer-Encapsulated Cell Therapy", *Neurosci. Biobehav. Rev.,* 16, pp. 437–447 (1992); D. F. Emerich et al., "Polymer-Encapsulated PC12 Cells Promote Recovery Of Motor Function In Aged Rats", *Exp. Neurol.,* 122, pp. 37–47 (1993). Indeed, encapsulated PC12 cell grafts survive for at least 6 months and continue to express tyrosine hydroxylase (TH) in guinea pigs without immunosuppression, supporting the motion that these cells can remain viable even following xenografting and can continue to synthesize dopamine if isolated from the host immune system. P. Aebischer et al., "Long-Term Cross-Species Brain Transplantation Of A Polymer-Encapsulated Dopamine-Secreting Cell Line", *Exo. Neurol.,* 111, pp. 269–273 (1991).

Recently, Aebischer and coworkers reported that implants of encapsulated PC12 cells can reverse motor deficits in monkeys rendered hemiparkinsonian with intracarotid n-methyl 4 phenyl 1,2,3,6, tetrahydropyridine (MPTP). Small pockets of TH-immunoreactive PC12 cells were observed for up to 6 months within capsules retrieved prior to sacrifice suggesting that dopamine secreted from the encapsulated cells mediated functional recovery in these animals. P. Aebischer et al., "Functional Recovery In Hemiparkinsonian Monkeys Transplanted With Polymer Encapsulated PC12 Cells", *Exp. Neurol.,* 126, pp. 151–158 (1994).

Although treatment of Parkinson's disease with dopamine has met with some success, the effects are transient at best. The human body tends to develop a resistance or insensitivity to dopamine replacement therapy and the degenerative processes of the disease continue. Accordingly, there is a need for a treatment for Parkinson's disease which will slow or prevent the progression of the disease.

SUMMARY OF THE INVENTION

This invention relates to implantation of encapsulated PC12 cells capable of slowing or preventing the degenerative processes of Parkinson's disease by releasing factors in addition to dopamine into individuals suffering from the disease. This restorative effect continues even after the encapsulated cells are removed from the patient's brain.

DETAILED DESCRIPTION OF THE INVENTION

Figure 1:
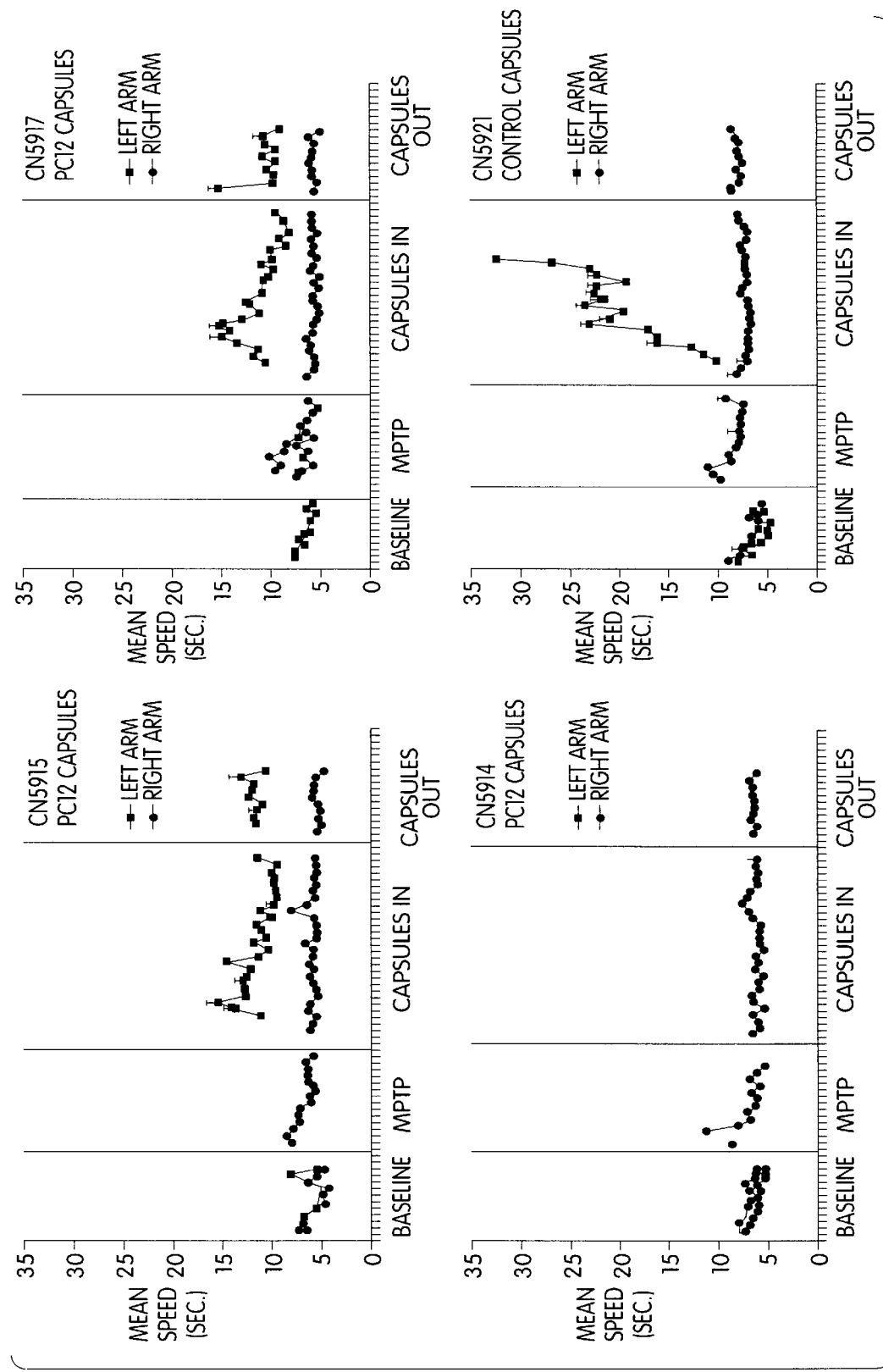
FIG. 1 shows the results of bilateral testing of fine motor coordination of the upper limbs in each monkey prior to and after MPTP treatment, during PC12 capsule implantation, and after removal of the capsules.

This invention relates to implantation of a biocompatible immunoisolatory capsule suitable for long-term implantation into individuals with Parkinson's disease, said capsule comprising (a) a core which contains PC12 cells, either suspended in a liquid medium or immobilized within a matrix material, and (b) a surrounding or peripheral region of permselective matrix or membrane (jacket) which does not contain isolated cells, which is biocompatible, and which is sufficient to protect isolated PC12 cells in the core from immunological attack. The encapsulated PC12 cells are capable of slowing or preventing the degenerative processes of Parkinson's disease by releasing factors other than dopamine. This restorative effect continues even after the encapsulated cells are removed from the patient's brain.

The term "individual" refers to an animal subject, preferably a primate and most preferably a human.

PC12 cells may be obtained from a variety of sources, including the American Type Tissue Culture in Rockville, Md. Preferably, the PC12 cells are isolated within a capsule whose core comprises a chitosan matrix or a nutrient medium, optionally containing a liquid source of additional factors to sustain cell viability and function, such as fetal bovine or equine serum.

The encapsulated PC12 cells should retain functionality for greater than three months in vivo and preferably for longer than six months and most preferably for longer than a year. In addition, the number of capsules implanted in the individual may be adjusted to achieve the desired therapeutic effect. Preferably, the implanted capsules are easily retrievable.

Many methods for encapsulating PC12 cells are known to those of skill in the art. See for example, D. F. Emerich et al., "Transplantation Of Polymer Encapsulate PC12 Cells: Use Of Chitosan As An Immobilization Matrix", *Cell Transplantation*, 2, pp. 241–249 (1993); S. R. Winn et al., "Behavioral Recovery Following Intrastriatal Implantation of Microencapsualted PC12 Cells", *Exp. Neurol.*, 113, pp. 322–329 (1991); D. F. Emerich et al., "Polymer-Encapsulated PC12 Cells Promote Recovery Of Motor Function In Aged Rats", *Exp. Neurol.*, 122, pp. 37–47 (1993); and C. B. Jaeger et al., "Growth Of Tumour Cell Lines In Polymer Capsules: Ultrastructure Of Encapsulated PC12 Cells", *Journal of Neurocytology*, 21, pp. 469–480 (1992).

The core of the immunoisolatory capsule should be constructed to provide a suitable local environment for the PC12 cells isolated therein. In some embodiments, the core may comprise a liquid medium sufficient to maintain the cells. In other embodiments, the core may comprise a gel matrix which immobilizes and distributes the cells, thereby reducing the formation of dense cellular agglomerations. The gel matrix may be composed of hydrogel or extracellular matrix components. Preferably, the matrix is a chitosan matrix as described in WO 94/07999, incorporated herein by reference.

The surrounding or peripheral region (jacket) of the capsule should be permselective, biocompatible, and preferably should isolate the PC12 cells from detrimental immunological attacks. It may be produced in such a manner that it is free of isolated cells, and completely surrounds (i.e., isolates) the core, thereby preventing contact between any PC12 cells in the core and the recipient's body.

The jacket should allow passage of substances up to a predetermined size, but prevent the passage of larger substances. More specifically, the surrounding or peripheral region may be produced in such a manner that it has pores or voids of a predetermined range of sizes; as a result, the capsule is permselective. The molecular weight cutoff (MWCO) selected for a particular capsule will be determined in part by the type and extent of immunological rejection it is anticipated will be encountered after the capsule is implanted and in part by the molecular size of the largest substance to be allowed to pass into and/or out of the capsule. For example, materials can be used to form permselective membranes or hydrogel matrices which allow passage of molecules up to about the size of 400 kD. In this instance, substances smaller than 400 kD can pass freely. It is also possible to form permselective matrices or membranes which allow passage of molecules up to about the size of about 150 kD and exclude larger molecules. Further, membranes or hydrogels which allow passage of molecules up to about the size of about 1,000 kD can be used; only very large substances, such as cells, will be excluded in this embodiment.

The term "biocompatible" refers collectively to both the intact capsule and its contents. Specifically, it refers to the capability of the implanted intact capsule and its contents to avoid detrimental effects of the body's various protective systems and remain functional for a significant period of time. In addition to the avoidance of protective responses from the immune system, or foreign body fibrotic response, "biocompatible" also implies that no specific undesirable cytotoxic or systemic effects are caused by the capsule and its contents such as would interfere with the desired functioning of the capsule or its contents.

The jacket of the capsule should be biocompatible. That is, it should not elicit a detrimental host response sufficient to result in rejection of the implanted capsule or to render it inoperable. Neither should the jacket elicit unfavorable tissue responses such as fibrosis. In addition, the external surface can be selected or designed in such a manner that it is particularly suitable for implantation at the selected site. For example, the external surface can be smooth, stippled or rough, depending on whether attachment by cells of the surrounding tissue is desirable. The shape or configuration can also be selected or designed to be particularly appropriate for the implantation site chosen.

The biocompatibility of the surrounding or peripheral region (jacket) may be produced by a combination of factors. Important for biocompatibility and continued functionality are capsule morphology, hydrophobicity and the absence of undesirable substances either on the surface of, or leachable from, the capsule itself. Thus, brush surfaces, folds, interlayers or other shapes or structures eliciting a foreign body response should be avoided. The capsule-forming materials should be sufficiently pure that unwanted substances do not leach out from the capsule materials themselves. Additionally, following capsule preparation, the treatment of the external surface of the capsule with fluids or materials (e.g. serum) which may adhere to or be absorbed by the capsule and subsequently impair capsule biocompatibility can be avoided.

The materials used to form the capsule should be substances selected based upon their ability to be compatible with, and accepted by, the tissues of the recipient of the implanted capsule. Substances should be used which are not harmful to the recipient or to the isolated biologically active moiety. Preferred substances include reversibly and irreversibly gellable substances (e.g., those which form hydrogels), and water-insoluble thermoplastic polymers. Particularly preferred thermoplastic polymer substances are those which are modestly hydrophobic, i.e. those having a solubility parameter as defined in Brandrup J., et al. *Polymer Handbook* 3rd Ed., John Wiley & Sons, NY (1989), between 8 and 15, or more preferably, between 9 and 14 $(Joules/m^3)^{1/2}$. The polymer substances should be chosen to have a solubility parameter low enough so that they are soluble in organic solvents and still high enough so that they will partition to form a proper membrane. Such polymer substances should be substantially free of labile nucleophilic moieties and be highly resistant to oxidants and enzymes even in the absence of stabilizing agents. The period of residence in vivo which is contemplated for the particular immunoisolatory capsule must also be considered. Substances must be chosen which are adequately stable when exposed to physiological conditions and stresses. There are many hydrogels and thermoplastics which are sufficiently stable, even for extended periods of residence in vivo, such as periods in excess of one or two years. Examples of stable materials include alginate (hydrogel) and polyacrilonitrile/polyvinylchloride ("PAN/PVC").

Substances used in preparing the biocompatible immunoisolatory capsule should be either free of leachable pyrogenic or otherwise harmful, irritating, or immunogenic substances or exhaustively purified to remove such harmful substances. Thereafter, and throughout the manufacture and maintenance of the capsule prior to implantation, great care should be taken to prevent the adulteration or contamination of the capsule with substances which would adversely affect its biocompatibility.

The exterior configuration of the capsule, including its texture, should be formed in such a manner that it provides an optimal interface with the tissues of the recipient after implantation. This parameter may be defined in part by the site of implantation. For example, if the capsule will reside in the peritoneal cavity of the recipient, its surface should be smooth. However, if it will be embedded in the soft tissues of the recipient, its surface can be moderately rough or stippled. A determining factor will be whether it is desirable to allow cells of the recipient to attach to the external surface of the capsule or if such attachment must be avoided. An open-textured or sponge-like surface may promote the ingrowth of capillary beds, whereas a smooth surface may discourage excessive overgrowth by fibroblasts. Excessive overgrowth by fibroblasts should be avoided, except where capillary undergrowth has occurred, as it may result in the deposition of a poorly-permeable basement membrane around the capsule and walling off of the isolated cells from contact with the recipient's body.

Certain capsule geometries have also been found to specifically elicit foreign body fibrotic responses and should be avoided. Thus capsules should not contain structures having interlayers such as brush surfaces or folds. In general, opposing capsule surfaces or edges either from the same or adjacent capsules should be at least 1 mm apart, preferably greater than 2 mm and most preferably greater than 5 mm. Preferred embodiments include cylinders, "U"-shaped cylinders, and flat sheets or sandwiches.

The jacket of the biocompatible immunoisolatory capsule can optionally include substances which decrease or deter local inflammatory response to the implanted capsule, and/or generate or foster a suitable local environment for the implanted cells or tissues. For example antibodies to one or more mediators of the immune response could be included. Available potentially useful antibodies such as antibodies to the lymphokines tumor necrosis factor (TNF), and to interferons (IFN) can be included in the matrix precursor solution. Similarly, an anti-inflammatory steroid can be included. Christenson, L., et al., *J. Biomed. Mat. Res.*, 23, pp. 705–718 (1989); Christenson, L., Ph.D. thesis, Brown University, 1989, incorporated by reference.

A biocompatible capsule will be suitable for long-term isolation of the PC12 cells from the various protective systems of the body. The term "protective systems" refers to the types of immunological attack which can be mounted by the immune system of an individual in whom the instant capsule is implanted, and to other rejection mechanisms, such as the fibrotic response, foreign body response and other types of inflammatory response which can be induced by the presence of a foreign object in the individuals' body.

Preferably, the jacket of the implanted capsule should be immunoisolatory. That is, it should protect the PC12 cells in the core of the capsule from the immune system of the individual in whom the capsule is implanted. It may do so (1) by preventing harmful substances of the individual's body from entering the core of the capsule, (2) by minimizing contact between the individual and inflammatory, antigenic, or otherwise harmful materials which may be present in the core and (3) by providing a spatial and physical barrier sufficient to prevent immunological contact between the isolated moiety and detrimental portions of the individual's immune system.

The thickness of this physical barrier can vary, but it should always be sufficiently thick to prevent direct contact between the cells and/or substances on either side of the barrier. The thickness of this region generally ranges between 5 and 200 microns; thicknesses of 10 to 100 microns are preferred, and thickness of 20 to 75 microns are particularly preferred.

The jacket of the implanted capsule can be made of a hydrogel matrix or of a different material, such as a thermoplastic membrane. It can also be made of a matrix-membrane composite, such that a permselective thermoplastic membrane having matrix-filled pores, is formed.

Suitably, the external jacket may be formed of a thermoplastic material known to be biocompatible, such as the ones described herein. In addition, other jackets which have been used in the microcapsule field may also be used herein, such as alginate, suitably cross-linked with a multivalent ion such as calcium.

Additionally, reinforcing structural elements can be incorporated into the capsule. These structural elements can be made in such a fashion that they are impermeable, and are appropriately configured to allow tethering or suturing of the capsule to the tissues of the recipient. In certain circumstances, these elements can act to securely seal the surrounding or peripheral region (e.g., at the ends of a cylindrical capsule, or at the edges of a disk-shaped capsule), completing isolation of the core materials (e.g., a molded thermoplastic clip). For many configurations, it may be desirable that these structural elements do not occlude a significant area of the permselective surrounding or peripheral region.

In one preferred embodiment, the implantable immunoisolatory capsule of the present invention is of a sufficient size and durability for complete retrieval after implantation. To be contrasted with such microcapsules, which have a typical maximum practical volume on the order of 1 μl, the preferred immunoisolatory capsule of the present invention is termed "macrocapsule". Such macrocapsules have a core of a preferable minimum volume of about 1 to 10 μl and depending upon use are easily fabricated to have a value in excess of 100 μl.

The encapsulated PC12 cells may be implanted into the brain of an individual suffering from Parkinson's disease by any method known in the art. See, for example, International patent publication WO 93/00127 and WO 93/00127.

EXAMPLE 1: Production of Hemiparkinsonian Monkeys

We used four male cynomologous monkeys, housed one per cage for the duration of the study on a 12 hr on/12 hr off lighting schedule with food and water available ad libitum. The level of care for these animals exceeded that recommended by the National Institutes of Health.

We made selective unilateral lesions of the substantia nigra according to procedures well known to those of skill in the art. Briefly, we first transquilized the monkeys with ketamine (10 mg/kg, im) and then induced anesthesia with isoflurane (1–2%). We positioned the animal in the supine position with the neck hyperextended and slightly turned left. Under sterile conditions, we used a number 15 blade to cut through the skin along the medial edge of the sternoclidomastoid muscle, opened the carotid sheath using fine iris scissors and identified the common carotid artery, internal jugular vein and vagus nerves. Further dissection superiorly exposed the carotid bifercation. We identified the external carotid artery with the superior thyroid artery seen branching distal to the bifercation. We then temporarily ligated the external carotid artery via the placement of an aneurysm clip.

We administered a previously mixed solution of 1-methyl-4-Ophenyl-1,2,3,6-tetrahydropyridine (MPTP) at a dosage of 0.4 mg/kg by drawing it into a 60 ml syringe. The syringe was attached to a 25 gauge butterfly needle via a three way stopcock. We inserted the needle into the common carotid artery in the direction opposite to blood flow and delivered the MPTP solution over 15 minutes (4 ml/min) during which time a characteristic tachycardia was noted. A 3 ml postflush of saline then ensued. We then removed the butterfly needle from the common carotid artery and a small piece of Gelfoam was used to apply focal pressure to the penetrated vessel. Finally, we removed the aneurysm clip from the external carotid artery and closed the musculature, subcutaneous tissues, and skin in a routine fashion.

EXAMPLE 2: Behavioral Analysis: Fine Motor Coordination in Hemiparkinsonian Monkeys We conducted bilateral testing of fine motor coordination of the upper limbs in each monkey using a food-pickup task (FIG. 1). We placed raisins within a 3×3 matrix of recessed food wells embedded in a Plexiglas board. The monkeys must reach out of a modified home cage to retrieve the fruit reward. We placed six raisins on the board for each trial and ascertained the time it took for the monkeys to retrieve all six raisins (speed of movement). Monkeys received 10 trials per arm in each test session with the arm being tested alternated on each trial. The test board is configured in such a manner that cross-over attempts with the unaffected arm is impossible and the monkeys can only retrieve the raisins with the arm being tested. We used an investigator blinded to the monkeys' experimental condition to assess the ability of each animal to perform this task. The assessments were carried out for 2 months pre-MPTP and for 3 months post-MPTP.

Prior to MPTP treatment, all monkeys readily learned the hand-reaching task and their performance with each hand quickly plateaued during the two month baseline testing period. Average performance with each hand ranged between 4–8 seconds per trial over each ten trial session. No monkey displayed a preference or superiority with one hand versus the other (FIG. 1).

Following MPTP treatment, three of the four monkeys failed to perform at all with their affected limb and lack of motor performance for these monkeys continued for at least three months (FIG. 1). One monkey (CN5917) displayed a brief impairment with the affected limb but returned to baseline performance within 4 weeks. At that time, this monkey received an additional 0.4 mg/kg intracartoid injection of MPTP. This monkey then failed to perform with his affected limb for the following 7 weeks of testing. The motor performance of the limb ipsilateral to the injection (contralateral to the disability) was generally unaffected by the MPTP treatment. Monkeys CN5915, CN5914, and 5921 all displayed a minor slowing in the performance of the task with the mean increase in time to perform the task ranging from 2–5 seconds per trial. On one test, monkey CN5914 did not perform the task with either limb.

EXAMPLE 3: Preparation of PC12 Capsules

We obtained rat adrenal pheochromocytoma PC12 from Dr. Lloyd Greene of Columbia University. We cultivated the PC12 cells in 500 ml spinner cultures at 80 RPM in a serum-free defined medium HL-1 (Ventrex, Inc., Portland, Me.) at 37° C. in a water-saturated, 7% $CO_2$ ambiant air atmosphere. We then harvested the cells by collecting spinner culture supernatant and centrifuging at 800 x g. Viability was assessed by exclusion of trypan blue and determined to be 88±4% prior to encapsulation.

We resuspended the cells in HL-1 at a concentration of $4 \times 10^7$ cells/ml and added an equal volume of solution containing 2% (w/v) of pH 6.7 low viscosity chitosan (PROTOSAN, chitosan chloride, Protan Biopolymer, Drammen, Morway), resulting in a final cell concentration of $2.0 \times 10^7$ cells/ml.

We produced individual capsules 12±1 mm in length as follows. Single skinned semipermeable hollow fiber membranes were spun from a 12.5% poly (acrylonitrile co-vinyl chloride) copolymer solution by a wet spinning technique. See, e.g., Cabasso, Hollow Fiber Membranes, Vol. 12, *Kirk-Othmer Encyclopedia of Chemical Technology*, Wiley, New York, 3rd ed. pp. 492–517 (1980). The resulting fibers had an inner diameter of about 500 microns and a wall thickness of about 65 microns. The fibers were loaded with the chitosan cell suspension according to methods substantially as described in International patent publication WO 92/19195. The capsules were prepared and hub sealed according to methods described in co-pending application 08/082,407. As controls, we used devices that contained the matrix material alone.

Prior to the placement of a silicon-based tube (i.e., tether) over the proximal loading port, we assayed the PC12 cell-loaded capsules under static incubation conditions to quantify L-dopa and dopamine release, as described further below. Following the assay procedure, we tethered the control and cell-loaded capsules by placing a 1.3–1.5 cm length of silicon tubing over the sealed loading port. We maintained the tethered capsules in vitro for 3–5 days prior to implantation.

EXAMPLE 4: Transplantation of the Capsules

Three months following the MPTP infusion, we tranquilized and reanesthetized the monkeys as before and placed them in a Kopf stereotaxic apparatus. Under sterile conditions, we made a U-shaped incision based on the midline exposing the skull overlying the right striatum. We then made a 2 cm x 3 cm carniotomy overlying the striatum using a high speed drill and the dura was reflected in a U-shaped manner. We stereotaxically placed two polymer capsule implants into the head of the right caudate nucleus and three capsules into the right putamen. All monkeys received the same number of capsules distrubuted in similar loci within the striatum. We cut the tether at the surface of the cortex to facilitate later identification and retrieval. We then reapproximated and sutured the dura and the skull cap back into place, sutured subcutaneous tissues with 4-0 Coated Vicryl inverted sutures and closed the skin with 4-0 Ethilon sutures in a routine fashion.

EXAMPLE 5: Behavioral Analysis of PC12-transplanted Monkeys

We assessed fine motor coordination of the monkeys as described in Example 2 for 6.5 months following transplantation of the capsules. We observed differential responses in limb use following transplantation of polymer capsules into the caudate nucleus and putamen (FIG. 1). Two monkeys which received encapsulated PC12 cells (CN5915 and CN5917) began to use their (left) arm on the side contralateral to the lesion and graft and began performing the hand reaching task about three weeks post-transplantation. These two monkeys continued to use the limb for the remainder of the 6.5 month post-transplantation period. The motor performance with this limb was slightly variable for the first three months post-transplantation. In contrast, motor function stabilized during the remaining three months and a consistent high level of performance on this task was observed. Indeed for both of these monkeys, the speed at which they were able to pick up the six food rewards with their affected limb was rapid (range 8–15 sec). It should be noted, however, that this level of performance was still impaired relative to baseline levels or relative to the intact arm. The encapsulated PC12 cell grafts did not alter the motor function in these animals on the side ipsilateral to the lesion.

In contrast to these monkeys, monkey CN5914 which also received encapsulated PC12 grafts into the caudate nucleus and putamen did not recover limb use during the post-transplantation period. Nor did these grafts alter motor performance in the unaffected arm. Subsequent analysis of the capsules retrieved from this monkey contianed very few viable PC12 cells which secreted negligible or undetectable levels of levodopa and dopamine, even under conditions of potassium stimulation (see Examples 7–8, infra).

Monkey CN5921 received control transplants of empty polymer capsules placed into the caudate nucleus and putamen. This animal displayed a transient recovery of function in the affected limb which soon dissipated. Over the 6.5 month post-transplantation period, the motor performance of this monkey progressively deteriorated in the affected limb. Indeed, this animal failed to use the impaired arm for the final seven weeks of testing post-transplantation. This waning of initial improvement followed a time course similar to that described for the closure of the blood-brain barrier following transplantation. Like monkeys receiving the PC12 cell implants, control grafts failed to influence motor performance in the nonaffected limb.

EXAMPLE 6: Removal of the Capsules and Behavioral Analysis Following Removal We retrieved all capsules 6.5 months following transplantation, as follows. Each monkey was again tranquilized, anesthetized, placed in the stereotaxic apparatus and draped in a sterile fashion as before. We cut the sutures which were used to resecure the skull cap with fine scissors and removed the skull cap using a high speed drill. The underlying dura was again incised in a U-shaped manner. We visualized the tethered portion of each capsule and removed them using fine microforceps. The dura and skull cap were then reattached as previously described and the skin closed using routine methods.

We continued to assess fine motor coordination of the monkeys by the method described in Example 2 for 2.5 months after removal of the capsules. Surprisingly, removal of the capsules in the two monkeys that had recovered limb use following transplantation (CN5915 and CN5917) failed to reinstate the MPTP-induced functional deficits in limb use. In fact, the motor performance in both animals was generally unaltered following removal of the grafts, with the performance on the hand-reach task being indistinguishable from that seen prior to graft withdrawal for most of the 10 week test period. Monkey CN5917 displayed a transient impairment which soon recovered back to the level of function seen just prior to implant removal.

The continued reversal of motor defects in these monkeys after removal of the capsules indicates that the dopamine secreted by the implanted cells is not solely responsible for the behavioral changes observed upon transplantion of the capsules, as was previously believed.

The monkey which received PC12 cell grafts but did not recover (CN5914) and the control grafted monkey (CN5921) were unaffected by graft retrieval. Moreover, performance with the unaffected limbs in all monkeys was not altered following the removal of the capsules.

EXAMPLE 7: Neuroanatomical Analysis of the Capsules

We analyzed the capsules in vitro following retrieval by fixing in 4% paraformaldehyde, rinsing in PBS and dehydrating up to 95% ethanol. We then added a 1:1 solution of glycol methacrylate (Historesin, Reichert-Jung, Cambridge Instruments) to the capsules for one hour. We replaced the 1:1 mixture with pure infiltration solution for a minimum of 2 hours. We then rinsed the capsules with the embedding solution, transferred them to flat molds, and embedded them in glycol methacrylate. We then made sections 5 $\mu$m thick (Reichert-Jung, Supercut microtome 2065), mounted the sections on glass slides and stained for hematoxylin and eosin.

We found few adhering host cells on the capsule surface. An abundance of viable PC12 cells, randomly distributed, were present throughout the capsules retrieved from the two primates which showed functional recovery (CN 5915 and CN5917). Hematoxylin and eosin stained sections showed several small (50 $\mu$m diameter) to medium (100 $\mu$m diameter) sized clusters of cells in each capsule, distributed along the entire length (12 nm) of the capsule. We occasionally observed areas of focal cell debris within the cores of the larger viable cell aggregates. We observed numerous mitotic figures throughout these capsules. In contrast, capsules retrieved from the primate which did not demonstrate functional recovery (CN5914) contained few, if any, viable PC12 cells.

EXAMPLE 8: Biochemical Analysis of the Capsules—Levodopa and Dopamine Levels We determined basal and potassium-evoked release of dopamine, levodopa, and dopamine metabolites for each of the PC12 cell loaded capsules both prior to transplantation and following capsule retrieval 6.5 months following grafting.

Three days after the encapsulation procedure, we washed free-floating capsules twice with 1 mL of HBSS HEPES buffered saline (containing 10 µM ascorbate) to remove residual culture medium. Sample capsules were incubated for 30 min (basal release) in 250 µL HBSS followed immediately by a 15 min incubation in HBSS containing 56 mM potassium (stimulated). All samples were protected from oxidation by the rapid addition of a citrate-reducing acidified buffer (CRAB) and yielded a stable sample preparation in 10 mM citric acid, 20 µM sodium metabisulfite, and 0.1N perchloric acid. Extended storage was at −80° C. Standards were prepared by diluting stock solutions in HBSS and stabilizing them with CRAB and 0.1N perchloric acid.

After removal of the capsules from the host striatum, we placed them in 1 ml of phosphate HBSS for approximately 30 min. The phosphate HBSS was removed, and 1 ml of HEPES-HBSS was placed on the capsules for an additional 30 min for basal and 15 min stimulated catecholamine analysis. After the catecholamine assay was completed, we placed the capsules in 4% paraformaldehyde for morphologic analysis.

Figure 2:
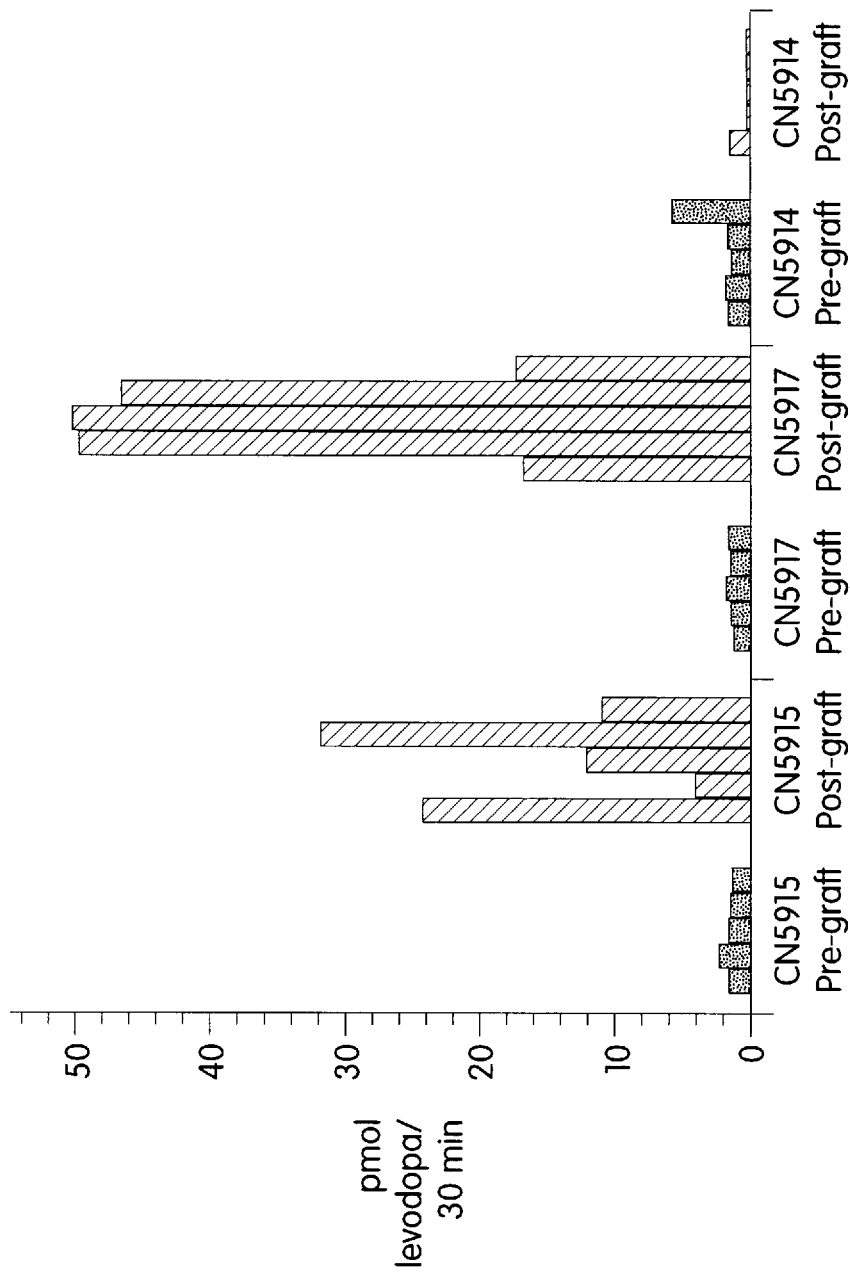
FIG. 2 shows pre and post-graft levels of levodopa release from the PC12 capsules.

We found that for all three monkeys receiving PC12 cell implants, relatively low levels of levodopa were released from the capsule at the time of implantation (FIG. 2). In contrast, basal levels of levodopa released from the PC12 cell loaded capsules were consistently high in the capsules retrieved from the two monkeys demonstrating a significant functional recovery following transplantation (CN 5915 and CN5917) with 9 of 10 capsules secreting >10 pmol levodopa/30 min (FIG. 2). Some of the retrieved capsules secreted high levels of levodopa with up to 45–50 pmol levodopa/30 being secreted in three of the PC12 cell loaded capsules.

In contrast to the two monkeys which exhibited a functional recovery, we found that the capsules from the one PC12 cell grafted monkey which did not display a functional recovery (CN5914) secreted extremely low levels of levodopa both prior to transplantation and 6.5 months post-transplantation.

In fact, levodopa levels were undetectable in 4 of the 5 capsules retrieved from this monkey just prior to sacrifice.

Figure 3:
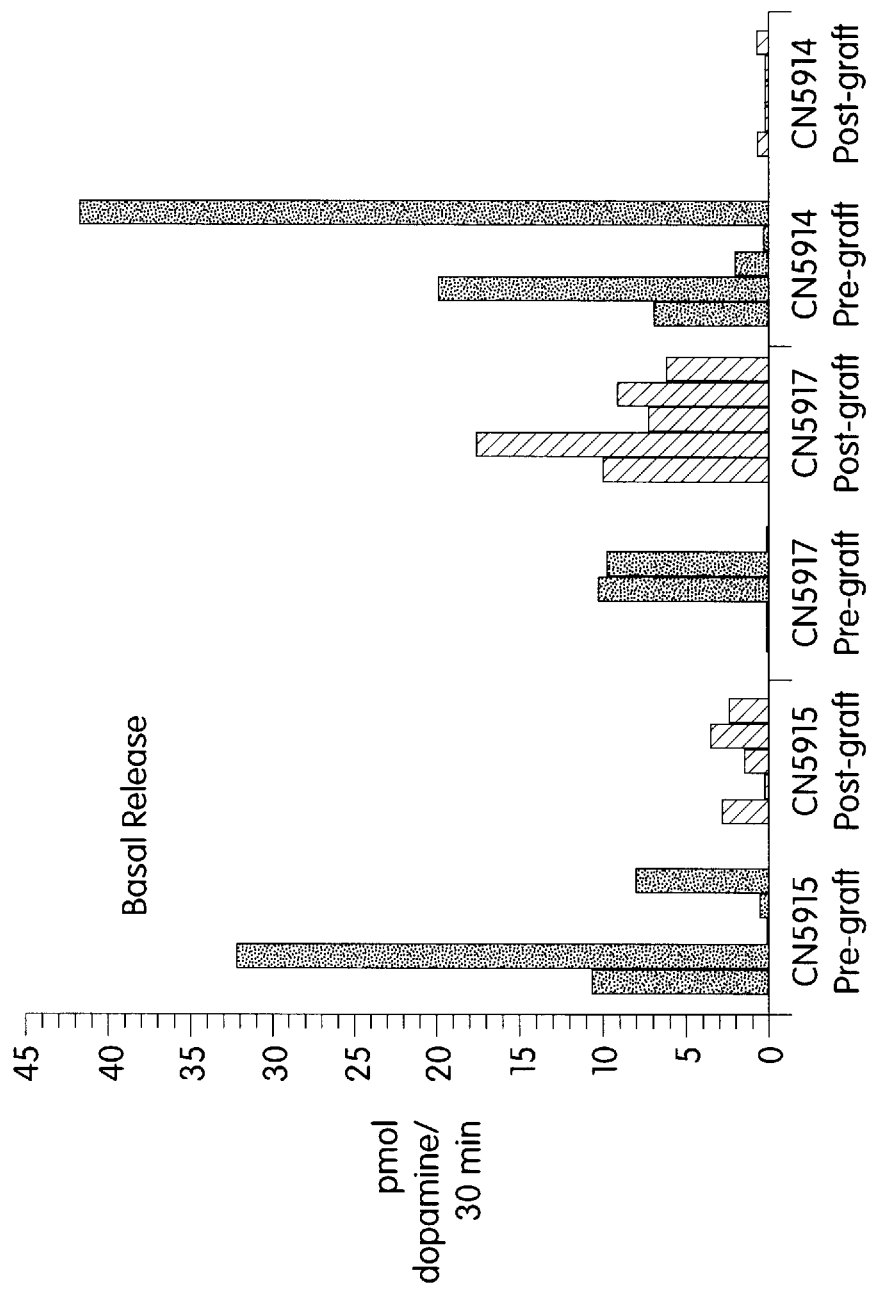
FIG. 3 shows pre and post-graft levels of dopamine release from the PC12 capsules.

While the general pattern for basal dopamine release was similar to that seen for levodopa, the secretion of dopamine was somewhat more variable. In the two monkeys that recovered limb use following transplantation, abundant levels of dopamine were still being released from 9 of 10 capsules 6.5 months following transplantation (FIG. 3). In some cases, the levels of dopamine being released were greater than that seen pre-implantation while other capsules secreted dopamine at a rate lower than that seen prior to grafting. In the monkey which did not recover, negligible levels of dopamine were secreted from all five capsules.

Figure 4:
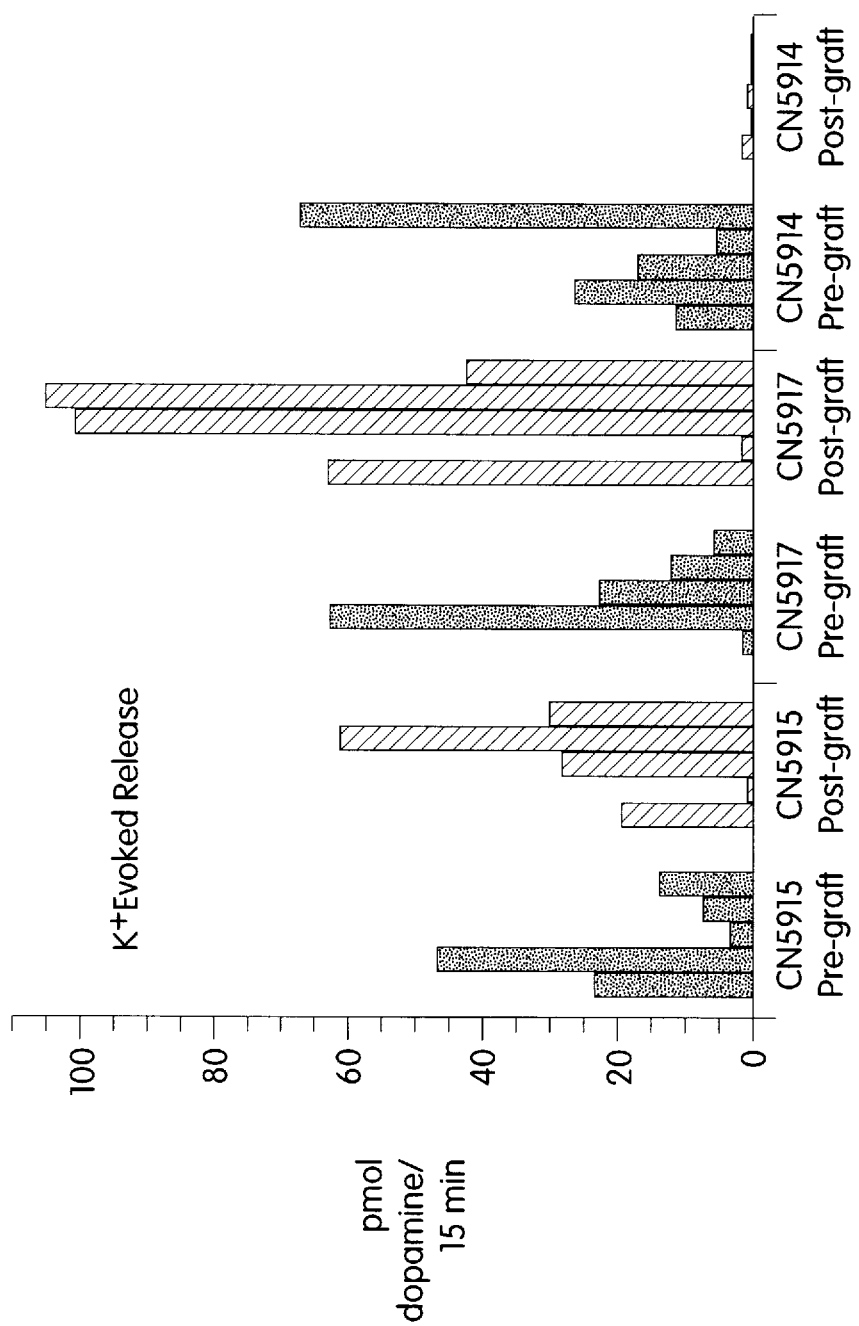
FIG. 4 shows pre and post-graft levels of potassium evoked dopamine release from the PC12 capsules.

We found that the level of dopamine secreted from the encapsulated PC12 cells was enhanced under conditions of potassium stimulation indicating that these cells were still capable of responding to this ionic challenge following grafting with up to a doubling of dopamine release following the administration of potassium (FIG. 4). It should be noted and the relative increase in dopamine release over basal levels is actually larger than that displayed due to the fact that we measured basal levels over 30 min. while we measured potassium-evoked release of dopamine over a 15 min. timespan. Again, the pattern of K+-evoked dopamine release was associated with the level of functional recovery displayed by the graft recipients. We observed high levels of K+-stimulated dopamine release in 8 of 10 capsules retrieved from the two monkeys displaying functional recovery following transplantation. In contrast, we observed negligible to undetectable levels of K+-stimulated dopamine release in the PC12 cell-grafted monkey which did not recover limb use following transplantation.

The pattern of dopamine metabolites secreted from the PC12 cell capsules mirrored that seen for levodopa and dopamine. Prior to transplantation, significant levels of homovanillic acid (HVA) and DOPAC were secreted from the PC12 cells. However, we observed significant levels of each metabolite only following retrieval of the capsule 6.5 months following transplantation from the two monkeys that recovered limb use following grafting (Table 1).

TABLE I

| Metabolites secreted from the encapsulated PC12 Cells | | |
|---|---|---|
| Animal number | Pregraft | Post-graft |
| HVA | | |
| CN5915 | 3.28 ± 1.31 | 8.0 ± 2.44 |
| CN5917 | 2.02 ± 0.58 | 28.2 ± 9.57 |
| CN5914 | 7.26 ± 4.6 | 0.96 ± 0.60 |
| DOPAC | | |
| CN5915 | 3.63 ± 1.78 | 7.67 ± 2.28 |
| CN5917 | 1.94 ± 0.55 | 31.8 ± 7.58 |
| CN5914 | 5.64 ± 3.43 | 1.31 ± 0.57 |

All data mean ± SEM pmol/30 min.

EXAMPLE 9: Neuroanatomical Assessment and Biochemical Analysis of the Host Striatum and Substantia Nigra Preparation of Tissues At the time of sacrifice, we anesthetized monkeys with pentobarbital (25 mg/kg, iv) and perfused transcardially with warm (100 ml) and then ice cold (400 ml) normal saline. We rapidly removed the brain from the calvaria and immersed it in ice cold saline for 10 min. We then placed the brain in a calibrated lucite brain slice apparatus with its inferior surface facing upwards. We sliced the brain in the coronal plane, from the frontal pole to the ventral diencephalon, into 4 mm tissue slabs. We similarly sliced the midbrain and brain stem in 8 mm thicknesses and placed the slices immediately in a 4% Zamboni's fixative. We then either immersion fixed in Zamboni's fixative or placed on an iced Petri dish alternating tissue slabs through the striatum. We then took tissue punches bilaterally through the caudate nucleus and putamen using an 18 gauge blunt needle, placed the punches in a 1.5 ml centrifuge tube and froze them on dry ice for neurochemical analyses of catecholamines within the host striatum. Once the punches were taken, we also immersion fixed the tissue slabs in Zamboni's fixative. Following 48 hr fixation, we cryoprotected the brains by immersion in a graded (10%–40%) sucrose/0.1M phosphate buffered saline (PBS) solution. We then stacked the tissue slabs upon one another and cut them on a sliding knife microtome while frozen (40 µm). We stored the tissue in a cryoprotectant solution prior to processing.

Immunohistochemistry

We processed sections for the immunohistochemical visualization of tyrosine hydroxylase (TH), serotonin, and glial fibrillary acidic protein (GFAP) using the labeled antibody procedure (23). Following 3×10 min washes in PBS plus 0.05% Triton-X (dilution media), we blocked background staining with a 1 hour incubation in a tris buffered saline solution containing 3% normal serum, 2% bovine serum albumin and 0.05% Triton-X. We then incubated the sections with either the polyclonal TH (1:2000; Eugene Tech), serotonin (Eugene Tech., 1:5000) or monoclonal GFAP (1:2000, Incstar. Corp.) primary antibodies for 48–72 h at room temperature. We then incubated sections for 1 h in either the goat antirabbit (TH, 5-HT) or horse antimouse (GFAP) biotinylated secondary antibodies [Vector Labs; 1:100]. After 12×10 min washes in dilution media, we placed the sections in the avidin-biotin (ABC "Elite"; Vector labs) substrate (1:000) for 75 min. We then washed the sections in a 0.1M imidazole/1.0M acetate buffer and reacted them in a chromagen solution containing the imidazole-acetate buffer, 2.5% nickel II sulfate, 0.05% 3,3' diaminobenzidine (DAB) and 0.005% $H_2O_2$. For controls, we processed tissue in an identical fashion except for employing the primary antibody solvent or an irrelevant IgG in lieu of the primary antibody. We mounted the sections on gelatin coated slides, dehydrated and coverslipped them with Permount. It is important to note that specificity for an immunocytochemical reaction product is not absolute. Regardless of the fact that deletion or substitution of the primary antibody may abolish immunoreactivity, the potential for antisera to react with structurally related antigens cannot be excluded. Thus a degree of caution is warranted and the term "immunoreactivity" in this application refers to "'like' immunoreactivity."

We used high performance liquid chromatography with electrochemical detection (LCEC) to detect L-Dopa, DA and the DA metabolites DOPAC and HVA. Isocratic LCEC consisted of an ESA coulometric multi-electrode detector model 5100, a Hitachi L-6200 pump, and a Waters WISP 712 satellite autoinjector. The mobile phase consisted of 75 mM monobasic sodium phosphate, 0.274 mM EDTA, 1,4 mM sodium octyl sulfonate, and 9% acetonitrile adjusted to pH 2,84 with HPLC grade phosphoric acid. We used triplicate standards to validate detection thresholds for L-Dopa, DOPAC (3,4-Dihydroxyphenylacetric acid), dopamine (dA), and HVA (homovanillic acid) with percent standard deviation ranges at threshold of 2–6%, 9–12%, 15–24%, and 6–17, respectively.

We stored tissue punches through the striatum in cryovials at −80° C. until assayed. We prepared tissue for analysis by placing it in 0.1N percloric acid chilled to 4° C. We subsequently homogenized the tissue using a polytron for 10–20 sec. We then placed the samples on ice. Samples were subsequently centrifuged at 4° C. for 5 min. We removed the supernate for catecholamine analysis and we used the pellet for protein analysis. We resuspended the pellet in 500 ul of 0.1N NaOH. We then spectrophotometrically determined the protein content and compared it to bovine serum albumin standards at 570 nm.

We thawed and spun samples for 1 min at 4° C. We determined catecholamine concentration by injecting 25 ul of the supernate onto an HPLC. We determined catecholamines by electrochemical detection (ESA). We calculated the concentration of catecholamines by comparing the electrochemical signal of each sample to that of a known set of standards that contained each of the catecholamines and their metabolites. Then, based on the amount of protein in each sample, we calculated the concentration of catecholamines and expressed that concentration as pmoles of catecholamine per milligram of protein.

We found that TH-immunostained sections through the midbrain revealed a significant degeneration (>85%) of TH-immunoreactive neurons within the substantia nigra pars compacta ipsilateral to the lesion relative to the contralateral side. We observed only a few TH-immunoreactive neurons ipsilateral to the MPTP infusion and these tended to be located within the dorsal (paranigralis) aspect of the nigra. We saw very few TH-immunoreactive neurons with the central and ventral portions of the A9 region. Conversely, this region displayed a very high density of GFAP-immunoreactive astrocytes as has been seen previously. In contrast, we found that the adjacent A10 ventral tegmental area was minimally affected with numerous TH-immunoreactive neurons seen bilaterally in all monkeys. Within the striatum, we observed a dense matting of TH-immunoreactive processes with the caudate nucleus, putamen, and nucleus accumbens in all animals contralateral to the MPTP lesion. In contrast, we observed a comprehensive loss of TH-immunoreactive fibers within the caudate nucleus and putamen ipsilateral to the MPTP injection. We found that TH-immunoreactivity was only modestly diminished within the nucleus accumbens ipsilateral to the lesion.

Nissl and GFAP-immunostained sections revealed the location of the polymer capsules and demonstrated that all and transplants were correctly placed within the head of the caudate and putamen. The grafts appeared to be very well tolerated within the host. In Nissl stained sections, a relatively normal cytoarchitectonic pattern of striatal neurons could be seen in close proximity to the implants. We observed very few macrophages, and those that we did see tended to be found directly within the transplant tract potentially invading this area at the time of graft retrieval. GFAP-staining revealed a dense astrocytosis within the tract of the capsules. However, we found that the density of GFAP-immunoreactive astrocytes quickly diminished distal to the central core of the graft. We observed the normal density of striatal astrocytes within 1000 $\mu$m of the implant site.

We extensively evaluated the pattern of TH-immunstaining within the caudate nucleus and putamen proximal to the implant sites for the potential sprouting of TH- and 5-HT-immunoreactive fibers. We found that the pattern of TH-immunoreactivity was similar in all animals regardless of whether they received control or PC12 cell implants and independent of whether motor function improved following the transplant. Long tracts created by the implant which often encompassed the dorsoventral extent of the caudate or putamen did not display a significant plexus of 7H-immunoreactive fibers proximal to the capsule tract. In some cases, we saw a few TH-immunoreactive fibers lining the perimeter of the implant site oriented in the dorsoventral direction. In other cases, we saw sparse collections of TH-immunoreactive fibers with swollen varicosities within the vicinity of the graft which may have been making an aborted attempt at sprouting towards the implant site. However, we observed processes which also displayed abnormal swollen varicosities coursing near the transplant site without any apparent preferential directionalty towards the graft. We observed serotonin-immunoreactive fibers bilaterally within the striatum. MPTP treatment did not appear to alter the morphologic appearance of the 5-HT innervation pattern of the caudate nucleus and putamen. MPTP treatment did not appear to alter the morphologic appearance of the 5-HT innervation pattern of the caudate nucleus and putamen. Furthermore, we observed a normal pattern of 5-HT-immunoreactive fibers proximal to the polymer encapsulated grafts.

Dopamine Levels Within The Host Striatum

Figure 5:
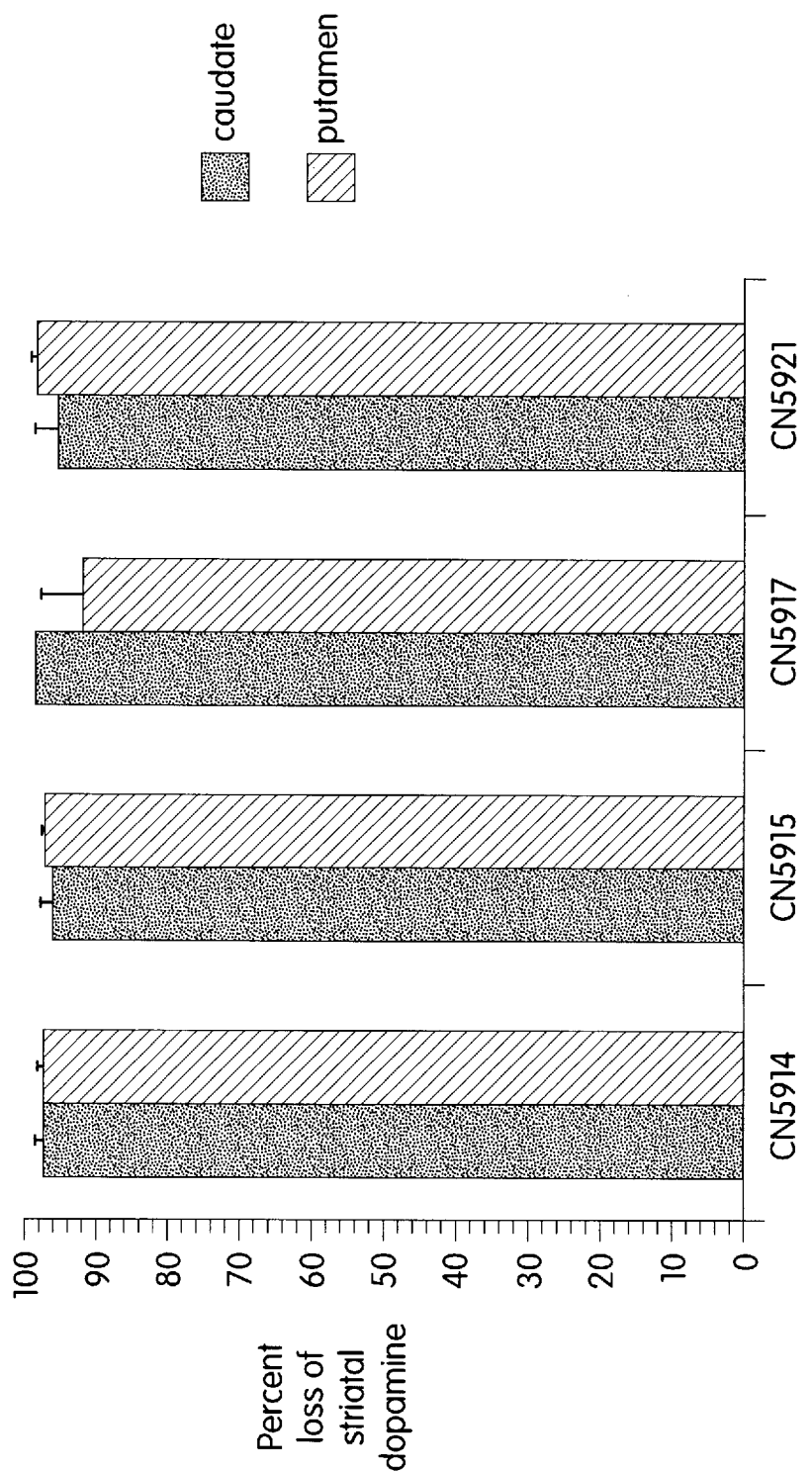
FIG. 5 shows the percent loss of striatal domaine in each monkey within the lesioned/grafted striatum relative to the intact contralateral side.

We took tissue punches through the caudate nucleus (n=3) and putamen (n=4) bilaterally from each monkey at the time of sacrifice. HPLC for dopamine revealed a comprehensive loss of dopamine within the lesioned/grafted striatum relative to the intact contralateral side (FIG. 5). For each monkey there was >95% loss of dopamine both within the caudate nucleus and putamen. CN5917 displayed a mean reduction of dopamine within the putamen of 90%. However, three of the four putamenal punches revealed reductions of >97% while the remaining putamenal punch only displayed a 70% reduction of dopamine. At the time of sacrifice, we took some of the punches quite proximal to a capsule tract which were evident with macroscopic observation. Even these punches revealed a comprehensive (>95%) loss of striatal dopamine supporting our neuroanatomical observations that transplants of encapsulated PC12 cells did not induce a dopaminergic host derived sprouting response. We observed extensive (>95%) reductions in HVA and DOPAC in all animals in both the caudate nucleus and putamen (data not shown).

We claim:

1. A method for slowing or preventing the progression of Parkinson's disease by implantation of a biocompatible immunoisolatory capsule suitable for implantation into individuals with Parkinson's disease for at least six months, said capsule comprising:

(a) a core which contains living PC12 cells capable of secreting a biologically active product or of providing a biological function to an individual; and (b) an external diffusional surface jacket surrounding said core which is biocompatible and which is sufficient to permit passage of substances between the individual and the core and to protect the isolated PC12 cells in the core from immunological attack.

2. The method according to claim 1, wherein the PC12 cells are suspended in a chitosan matrix.

3. The method according to claim 1 or claim 2, wherein the external jacket is a PAN/PVC membrane.

* * * * *